US011471661B2

(12) United States Patent
Mehaffey et al.

(10) Patent No.: US 11,471,661 B2
(45) Date of Patent: Oct. 18, 2022

(54) VENTRICULAR ASSIST DEVICE STENT, VENTRICULAR ASSIST DEVICE, AND RELATED METHODS THEREOF

(71) Applicant: University of Virginia Patent Foundation, Charlottesville, VA (US)

(72) Inventors: James Hunter Mehaffey, Charlottesville, VA (US); Mark Roeser, Charlottesville, VA (US); John A. Kern, Charlottesville, VA (US); Irving L. Kron, Charlottesville, VA (US); Gorav Ailawadi, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 169 days.

(21) Appl. No.: 16/098,579

(22) PCT Filed: May 4, 2017

(86) PCT No.: PCT/US2017/031027
§ 371 (c)(1),
(2) Date: Nov. 2, 2018

(87) PCT Pub. No.: WO2017/192832
PCT Pub. Date: Nov. 9, 2017

(65) Prior Publication Data
US 2019/0143019 A1 May 16, 2019

Related U.S. Application Data

(60) Provisional application No. 62/437,089, filed on Dec. 21, 2016, provisional application No. 62/332,577, filed on May 6, 2016.

(51) Int. Cl.
*A61M 60/17* (2021.01)
*A61M 60/148* (2021.01)
(Continued)

(52) U.S. Cl.
CPC .............. *A61M 60/148* (2021.01); *A61F 2/82* (2013.01); *A61F 2/848* (2013.01); *A61F 2/95* (2013.01);
(Continued)

(58) Field of Classification Search
CPC ...... A61F 2/2418; A61F 2/243; A61F 2/2427; A61F 2250/0039; A61F 2250/006; A61M 60/122; A61M 60/148; A61M 60/17
See application file for complete search history.

(56) References Cited

U.S. PATENT DOCUMENTS

| 5,415,664 A | 5/1995 | Pinchuk |
| 5,827,171 A | 10/1998 | Doback, III et al. |

(Continued)

FOREIGN PATENT DOCUMENTS

| JP | 2005080991 | 3/2005 |
| JP | 2005066013 | 3/2015 |

(Continued)

OTHER PUBLICATIONS

Kapelios et al., "Late-onset right ventricular dysfunction after mechanical support by a continuous-flow left ventricular assist device", Journal of Heart and Lung Transplantation, 2015, pp. 1604-1610, vol. 34, Iss. 12.

*Primary Examiner* — Michael J D'Abreu
(74) *Attorney, Agent, or Firm* — Robert J. Decker

(57) ABSTRACT

A method of assisting a heart for the operation of a ventricular assist device comprising the steps of implanting a cannula to the heart and deploying a stent within a left ventricle, a right ventricle, a left atrium, or a right atrium of the heart. The stent may be transferable from a first compact configuration to a second open configuration to facilitate implantation. The stent may also have a flared distal end to assist with alignment, positioning, and prevent outgrowth.

15 Claims, 10 Drawing Sheets

(51) Int. Cl.
  *A61F 2/848* (2013.01)
  *A61F 2/82* (2013.01)
  *A61M 60/122* (2021.01)
  *A61M 60/857* (2021.01)
  *A61F 2/95* (2013.01)
  *A61F 2/07* (2013.01)

(52) U.S. Cl.
  CPC ........ *A61M 60/122* (2021.01); *A61M 60/857* (2021.01); *A61F 2/07* (2013.01); *A61F 2250/0039* (2013.01)

(56) References Cited

U.S. PATENT DOCUMENTS

| | | | |
|---|---|---|---|
| 6,673,042 | B1 | 1/2004 | Samson et al. |
| 6,817,836 | B2 | 11/2004 | Nose et al. |
| 7,156,873 | B2 | 1/2007 | Nose et al. |
| 7,175,588 | B2 | 2/2007 | Morello |
| 7,284,956 | B2 | 10/2007 | Nose et al. |
| 7,396,327 | B2 | 7/2008 | Morello |
| 2004/0093058 | A1 | 5/2004 | Cottone et al. |
| 2005/0033107 | A1 | 2/2005 | Tsubouchi |
| 2006/0229488 | A1 | 10/2006 | Ayre et al. |
| 2006/0241335 | A1 | 10/2006 | Benkowski et al. |
| 2006/0293698 | A1 | 12/2006 | Douk |
| 2007/0049787 | A1 | 3/2007 | Nose et al. |
| 2007/0088436 | A1 | 4/2007 | Parsons et al. |
| 2007/0156233 | A1 | 7/2007 | Kapadia et al. |
| 2007/0244545 | A1 | 10/2007 | Birdsall et al. |
| 2008/0183273 | A1 | 7/2008 | Mesana et al. |
| 2008/0243224 | A1 | 10/2008 | Wallace et al. |
| 2008/0255653 | A1 | 10/2008 | Schkolnik |
| 2008/0306329 | A1 | 12/2008 | Lu et al. |
| 2010/0168848 | A1 | 7/2010 | Horvath et al. |
| 2010/0197994 | A1 | 8/2010 | Mehmanesh |
| 2011/0124950 | A1 | 5/2011 | Foster |
| 2012/0143141 | A1 | 6/2012 | Verkaik et al. |
| 2012/0150274 | A1 | 7/2012 | Shalev et al. |
| 2012/0209376 | A1 | 8/2012 | Hauser et al. |
| 2014/0100413 | A1 | 4/2014 | Casas et al. |
| 2014/0107399 | A1 | 4/2014 | Spence |
| 2014/0179993 | A1 | 6/2014 | Alexander et al. |
| 2015/0038770 | A1 | 2/2015 | Colella |
| 2015/0306290 | A1 | 10/2015 | Rosenberg et al. |
| 2015/0367048 | A1 | 12/2015 | Brown et al. |
| 2016/0058930 | A1 | 3/2016 | Medvedev |
| 2017/0290967 | A1 * | 10/2017 | Botterbusch .............. A61F 2/82 |

FOREIGN PATENT DOCUMENTS

| | | | |
|---|---|---|---|
| WO | WO 2005/094279 | 10/2005 | |
| WO | WO 2010/046895 | 4/2010 | |
| WO | WO-2011057087 A1 * | 5/2011 | ........... A61F 2/2418 |
| WO | WO 2014/207225 | 12/2014 | |
| WO | WO 2014/085806 | 10/2015 | |

* cited by examiner

VENTRICULAR ASSIST DEVICE STENT, VENTRICULAR ASSIST DEVICE, AND RELATED METHODS THEREOF

RELATED APPLICATIONS

The present application is a national stage filing of International Application No. PCT/US2017/031027, filed May 4, 2017, which claims benefit of priority under 35 U.S.C § 119 (e) from U.S. Provisional Application Ser. No. 62/332,577, filed May 6, 2016, entitled "Ventricular Assist Device Anti-Suction Intra-cardiac Cage Device" and U.S. Provisional Application Ser. No. 62/437,089, filed Dec. 21, 2016, entitled "Ventricular Assist Device Anti-Suction Intra-cardiac Cage Device"; the disclosures of which are hereby incorporated by reference herein in their entirety.

FIELD OF THE INVENTION

The present invention relates generally to ventricular assist devices, and more particularly to stents used in the heart that improve the performance of ventricular assist devices.

BACKGROUND

A ventricular assist device ("VAD") is an electromechanical circulatory device that may be used to partially or completely replace the function of a failing heart.

As an example, a VAD may be used to help supplement the heart's pumping action both during and after certain kinds of surgery, in situations where a complete cardiopulmonary bypass (using a heart-lung machine) is neither needed nor advisable in light of the serious side effects associated therewith. VADs typically comprise a pair of cannulae or other tubing and some sort of pump operably connected to the cannulae. In use, the cannulae are attached to either the left side of the heart (i.e., a left ventricular assist device, LVAD) or to the right side of the heart (i.e., a right ventricular assist device, RVAD) "in parallel" (i.e., the pump supplements the heart's pumping action but does not completely bypass it, and the pump is activated). Alternatively, a pump may be directly implanted into the body.

Current VADs suffer from several major problems: suction events, adverse remodeling of the heart, ingrowth of heart tissue on the inflow cannula, and poor alignment of the inflow cannula within the heart. All of these problems present potentially life-threatening events in patients with a VAD and represent an obstacle to widespread advancement for use more common use, and also for use in the right ventricle, atrial, and pediatric uses. Current VAD devices and methods primarily address the problem of suction events with specific pump control mechanisms such as adjusted flow rate or frequency. However, these methods do not adequately address all problems. The present inventors submit that an intra-cardiac stent attached to the inflow cannula would ameliorate these adverse events by maintaining the cavity in normal configuration, preventing collapse, ensuring optimal heart geometry and flow properties, and/or providing a barrier to prevent ingrowth.

An aspect of an embodiment of the present invention approach presents a major advancement in VAD technology that will provide the opportunity for increased application.

OVERVIEW

An aspect of an embodiment of the present invention ameliorates one or more of the problems of suction events, adverse remodeling of the heart, ingrowth of heart tissue on the inflow cannula of a VAD, and poor alignment of the inflow cannula within the heart by providing a stent within a left ventricle, right ventricle, left atrium, and/or right atrium of the heart.

An aspect of an embodiment of the invention provides method of assisting a heart for the operation of a VAD that comprises implanting an inflow cannula to the heart and deploying a stent within a left ventricle, right ventricle, left atrium, or right atrium of the heart. The VAD inflow cannula may be implanted using a sewing right affixed to the heart. The stent may be deployed through a sewing ring, through the inflow cannula, or any other suitable implantation method including percutaneous after the operation. This method would involve a catheter-based approach entering the left side of the heart trans-septally. The stent may be connected to the inflow cannula, or it may be free-floating within the heart. The stent may be transferable between a first compact configuration for implantation and a second open configuration for use in the heart. The stent in the second open configuration may enable the stent to do one or more of cause the inflow cannula to maintain better alignment with a mitral valve, obstruct the collapse of the left ventricle, right ventricle, left atrium, or right atrium of the heart so as to prevent suction events, reduce adverse remodeling of a right ventricle of the heart, or reduce ingrowth of heart tissue on the inflow cannula. The stent may have a flared portion maintained around or outside of the inflow cannula. The stent may comprise a wire, which may be substantially contiguous. The stent may comprise one or more of nickel-titanium alloy, stainless steel, silicone, polyester, PTFE, or polypropylene.

Another aspect of an embodiment of the invention provides a stent for assisting the heart during operation of a VAD. The stent may comprise a central axis running along a length of the stent, a distal portion, a proximal portion opposite the distal portion, wherein the distal portion having a minimum radius from the central axis, and a first center portion and a second center portion. The first center portion may have a minimum radius from the central axis. The second center portion may have a maximum radius from the central axis. The first center portion and the second center portions may be in between the distal portion and the proximal portion along the central axis. The first center portion may be adjacent to the proximal portion and the second center portion may be adjacent to the distal portion. The maximum radius of the second center portion from the central axis may be smaller than the minimum radius from the central axis of the first center portion and the minimum radius of the distal portion such that the distal portion is in a flared configuration.

The stent may be transferable between a first compact configuration for implantation and a second open configuration for use in the heart. The stent in the first compact configuration may be deployable through an inflow cannula of a VAD or through a sewing ring affixed to the heart. The stent in the second open configuration may enable the stent to do one or more of cause the inflow cannula to maintain better alignment with a mitral valve, obstruct the collapse of the left ventricle, right ventricle, left atrium, or right atrium of the heart so as to prevent suction events, reduce adverse remodeling of a right ventricle of the heart, or reduce ingrowth of heart tissue on the inflow cannula. The stent may have a flared portion maintained around or outside of the inflow cannula. The stent may comprise a wire, which may be substantially contiguous. The stent may comprise one or more of nickel-titanium alloy, stainless steel, silicone, polyester, PTFE, or polypropylene.

The stent may be a component of a VAD that further comprises an inflow cannula. The stent may be affixed to the inflow cannula. The stent may be configured to interface with the inflow cannula, but not be affixed thereto. The stent may not be affixed to the inflow cannula.

An aspect of an embodiment of the present invention provides a method (and related device or system) of assisting a heart for the operation of a ventricular assist device comprising the steps of implanting a cannula to the heart and deploying a stent within a left ventricle, a right ventricle, a left atrium, or a right atrium of the heart. The stent may be transferable from a first compact configuration to a second open configuration to facilitate implantation. The stent may also have a flared distal end to assist with alignment, positioning, and prevent outgrowth.

These and other objects, along with advantages and features of various aspects of embodiments of the invention disclosed herein, will be made more apparent from the description, drawings and claims that follow.

BRIEF DESCRIPTION OF THE DRAWINGS

The foregoing and other objects, features and advantages of the present invention, as well as the invention itself, will be more fully understood from the following description of preferred embodiments, when read together with the accompanying drawings.

The accompanying drawings, which are incorporated into and form a part of the instant specification, illustrate several aspects and embodiments of the present invention and, together with the description herein, serve to explain the principles of the invention. The drawings are provided only for the purpose of illustrating select embodiments of the invention and are not to be construed as limiting the invention.

DETAILED DESCRIPTION OF EXEMPLARY EMBODIMENTS

Figure 1:
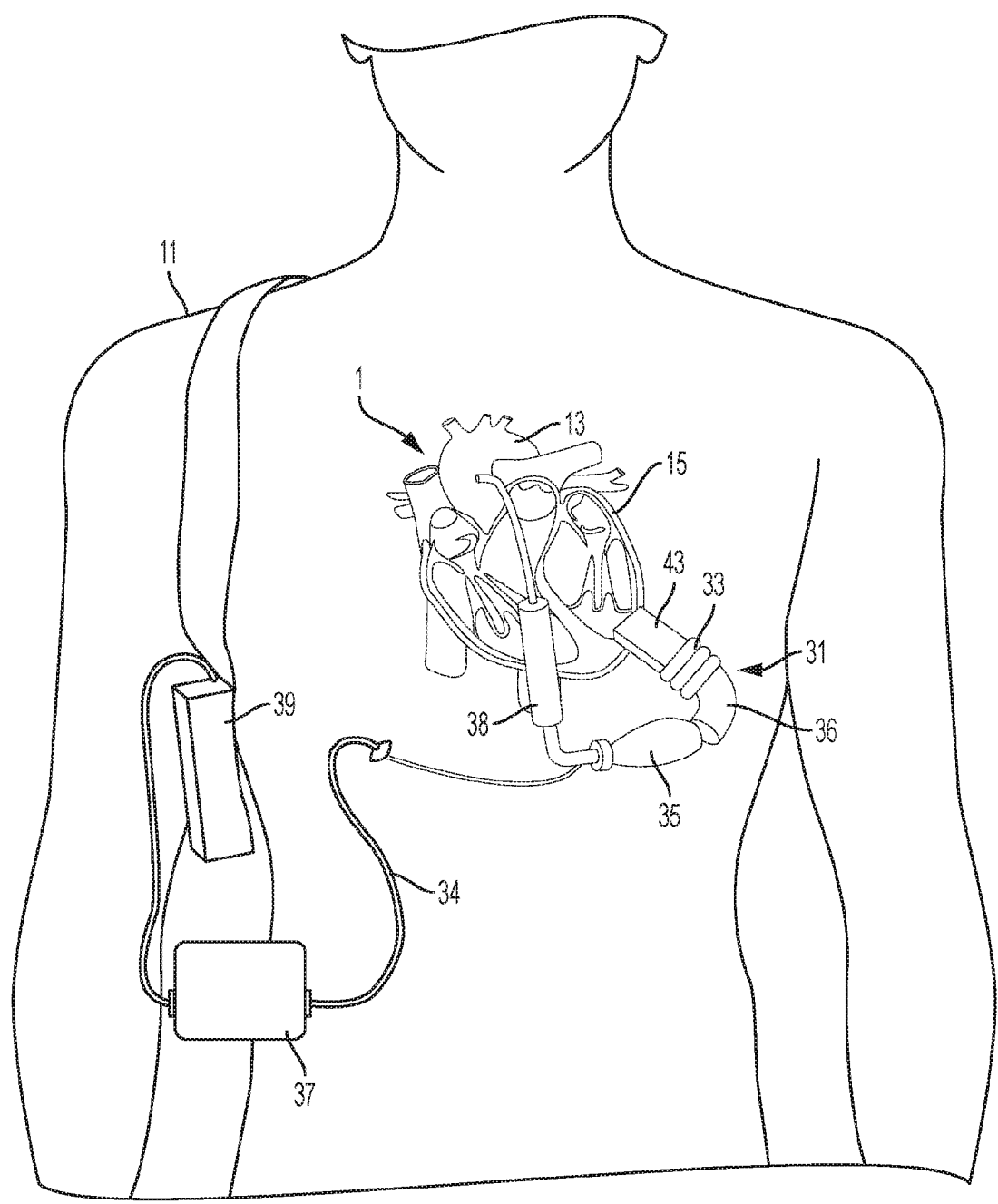
FIG. 1 schematically illustrates a ventricular assist device (VAD).

Although example embodiments of the present disclosure are explained in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

Some references, which may include various patents, patent applications, and publications, are cited in a reference list and discussed in the disclosure provided herein. The citation and/or discussion of such references is provided merely to clarify the description of the present disclosure and is not an admission that any such reference is "prior art" to any aspects of the present disclosure described herein. In terms of notation, "n" corresponds to the nth reference in the list. All references cited and discussed in this specification are incorporated herein by reference in their entireties and to the same extent as if each reference was individually incorporated by reference.

A detailed description of aspects of the present disclosure will now be provided with reference to the accompanying drawings. The drawings form a part hereof and show, by way of illustration, specific embodiments or examples. In referring to the drawings, like numerals represent like elements throughout the several figures.

Figure 2:
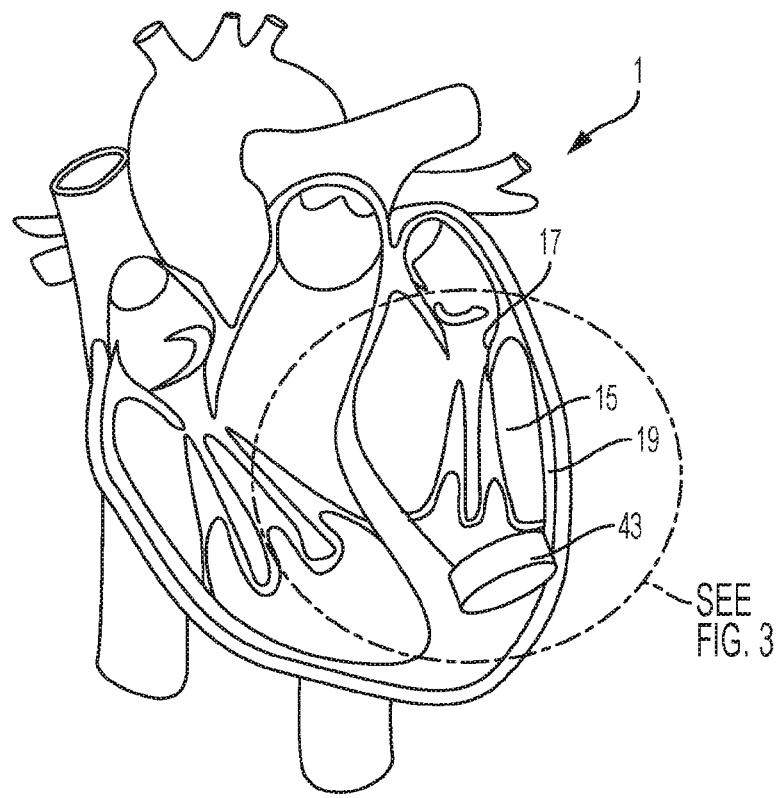
FIG. 2 schematically illustrates a heart with a sewing ring affixed thereto.
Figure 5:
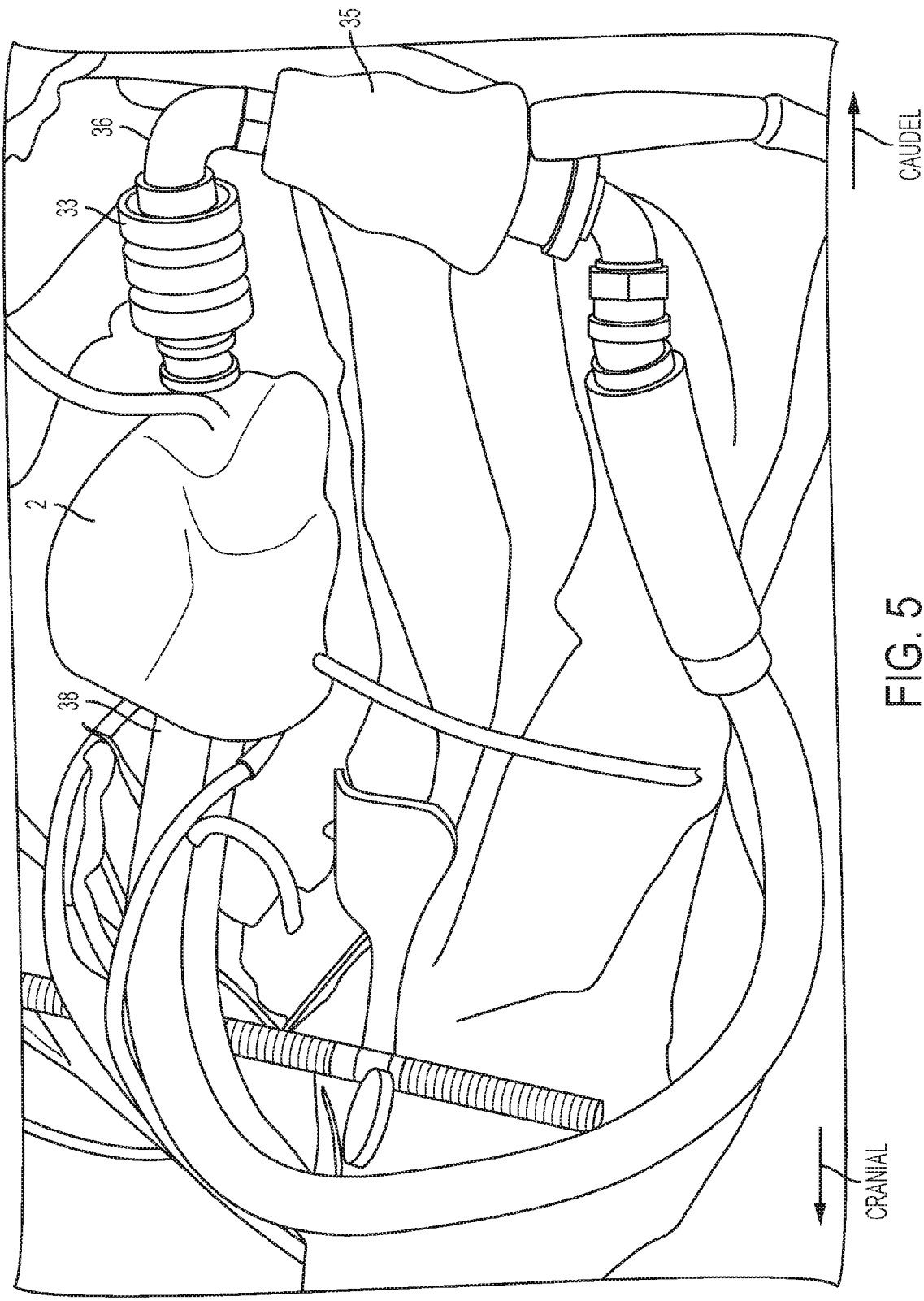
FIG. 5 schematically illustrates a ventricular assist device (VAD) in communication with a heart of a swine.

FIGS. 1 and 5 schematically illustrate an exemplary embodiment of a ventricular assist device ("VAD") 31 for use with a heart 1 of a subject or patient 11. For example, the heart 1 includes a left ventricle ("LV") 15 and an ascending thoracic aorta 13. A cannula 32 of the VAD 31 is implanted into the LV 15 of the heart 1 through sewing ring 43 for assistance with pumping. In operation, the cannula 32 is connected to a manifold 33 of the VAD 31, which is connected at an opposite end to an inflow conduit 36 of the VAD 31. Pump 35 of the VAD 31 is connected to the inflow conduit 36, and is used to assist in pumping blood from the LV 15 through the cannula 32, the manifold 33, and the inflow conduit 36 through the outflow conduit 38 of the VAD 31 into the ascending thoracic aorta 13 or other intended location. The operation of the pump 35 is controlled by controller 37 of the VAD 31 via communication along cable 34. In some embodiments, the cable may carry signals from a sensor in the pump or other suitable component of the VAD 31, or the heart (not shown) to the controller 37, and the controller may operate the pump based at least in part on the information provided by the sensor. It should be understood that the sensor may comprise one or more sensing elements that communicate one or more of pressure information, flow rate information, or any other information pertinent to operation of the VAD 31. FIG. 2 schematically illustrates a detailed view of the heart 1 without the stent 41. While FIGS. 1 and 2 illustrate the use of the VAD 31 in the LV 15 of the heart 1, it should be understood that the VAD 31 can be used in other parts of the heart 1, such as a right ventricle, left atrium, or right atrium.

Figure 6:
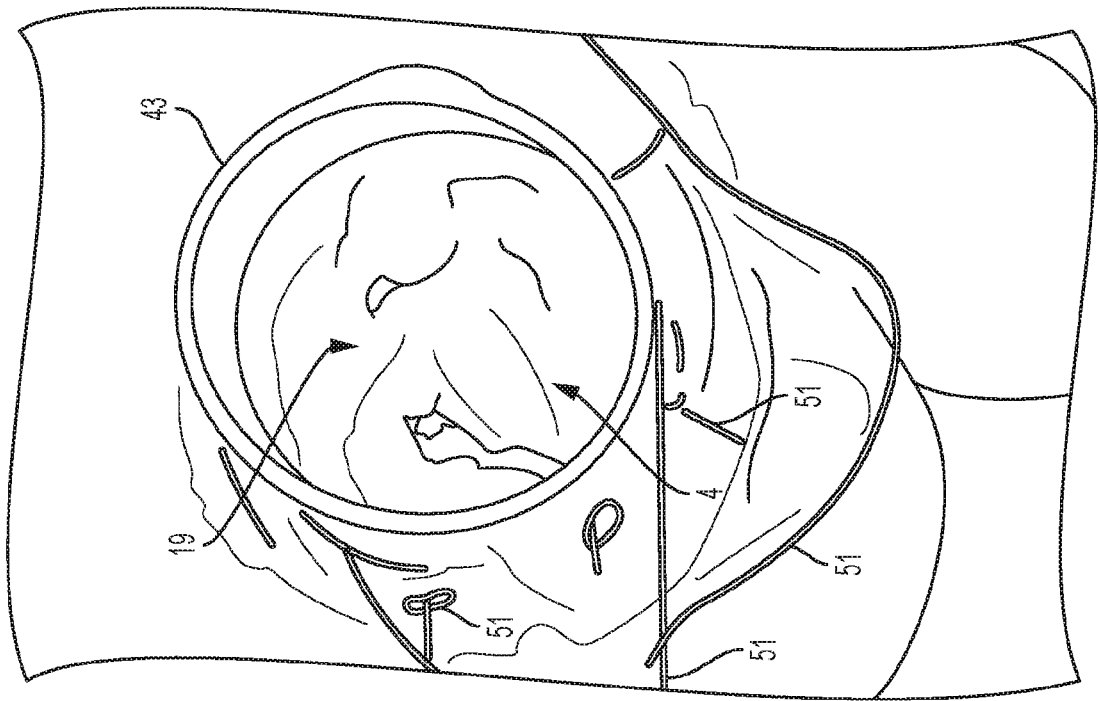
FIG. 6 schematically illustrates a ventricle of a heart in a collapsed configuration.

A number of problems arise with the use of the VAD 31 of FIGS. 1 and 2. First, ventricular suction events or ventricular collapses present major obstacles for advancement of VAD technology. FIG. 6 schematically illustrates a collapsed LV 4 as viewed through the sewing ring 43, which is affixed to the heart using sutures 41. As shown in FIG. 6, the walls of the collapsed LV 4 are in a compact or collapsed state, which, during operation of the heart, would cause a suction event. Current techniques to alleviate this problem include algorithm based computer programs to attenuate these events by decreasing flow rate by varying the operation of pump 35 when low ventricular pressure is sensed. However, such techniques require complicated detection and operation algorithms, and do not ameliorate the additional problems identified herein.

Second, as shown in FIG. 1, the cannula 32 can settle into a position of poor alignment with the mitral valve 17. While a cannula 32 in an aligned position with mitral valve 17 produces laminar flow, which serves for more efficient and beneficial operation of the VAD 31, a cannula 32 that is in an unaligned position with mitral valve 17 produces turbulent flow, which can cause unnecessary wear and reduce the efficiency and effectiveness of the VAD 31. Reducing the incidence of misalignment of the cannula 32 can help to avoid resulting hospital visits and exploratory surgery.

Third, implantation and use of a VAD 31 can cause the heart 1 to twist and can also cause portions of the heart 1 to atrophy or change in geometry. For example, when the VAD 31 is used to assist the LV 15, one or more of twisting of the heart 1 and changed geometry of LV 15 can cause adverse remodeling or atrophy of right ventricle of the heart 1. This adverse remodeling and/or atrophy geometry can reduce the effectiveness and/or longevity of VAD 31, thereby reducing patient outcomes. Recent studies have described late right ventricular dysfunction after left ventricular assist device implantation affecting as many as 40% of patients on mechanical circulatory support for more than one year. This results in worse outcomes after transplantation and worse long-term survival. Positioning problems are more acute when minimally invasive procedures are used.

Finally, prolonged use of the VAD 31 can present problems with ingrowth of heart tissue onto the cannula 32. Such ingrowth can impede the operation of the VAD 31. This problem can go on to cause pump thrombosis and complete failure requiring reoperation and pump exchange. While proper selection of materials and manufacturing methods for the cannula 32 can reduce the incidence of ingrowth, the problem can still persist.

In an aspect of an embodiment of the invention, a stent 41 is implanted into a portion of the heart 1 so as to ameliorate one or more of the problems of ventricular collapse, suction events, poor alignment of the cannula 32 in the heart 1, atrophy of a portion of the heart 1, adverse remodeling of the heart 1, and ingrowth of heart tissue. The device structure, geometry, composition, and interfacing characteristics with the heart 1 and/or the cannula 32 may vary as discussed and disclosed herein.

Figure 3:
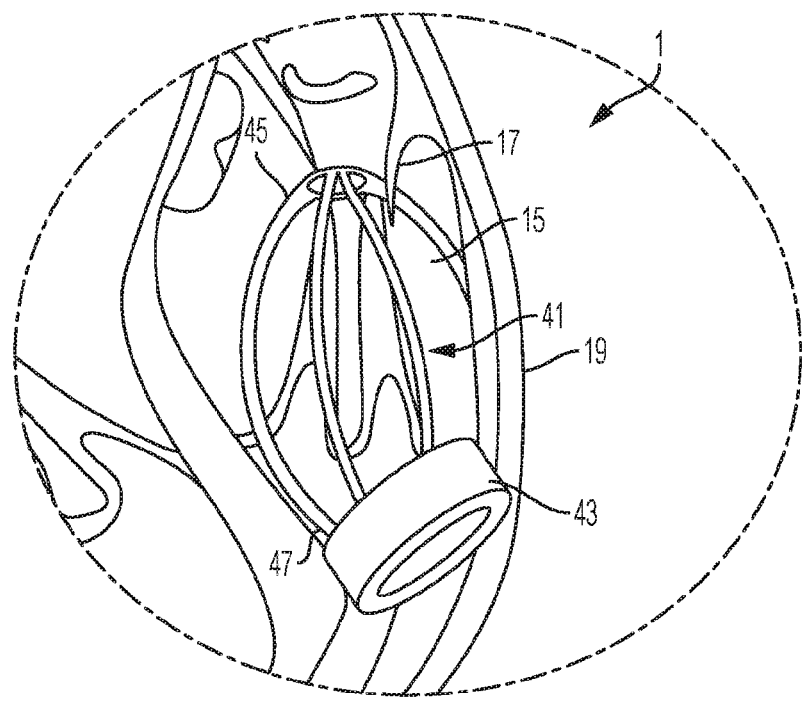
FIG. 3 schematically illustrates an enlarged partial view of a heart shown in FIG. 2 with a ventricular assist device (VAD) stent according to an aspect of an embodiment of the present invention.
Figure 4:
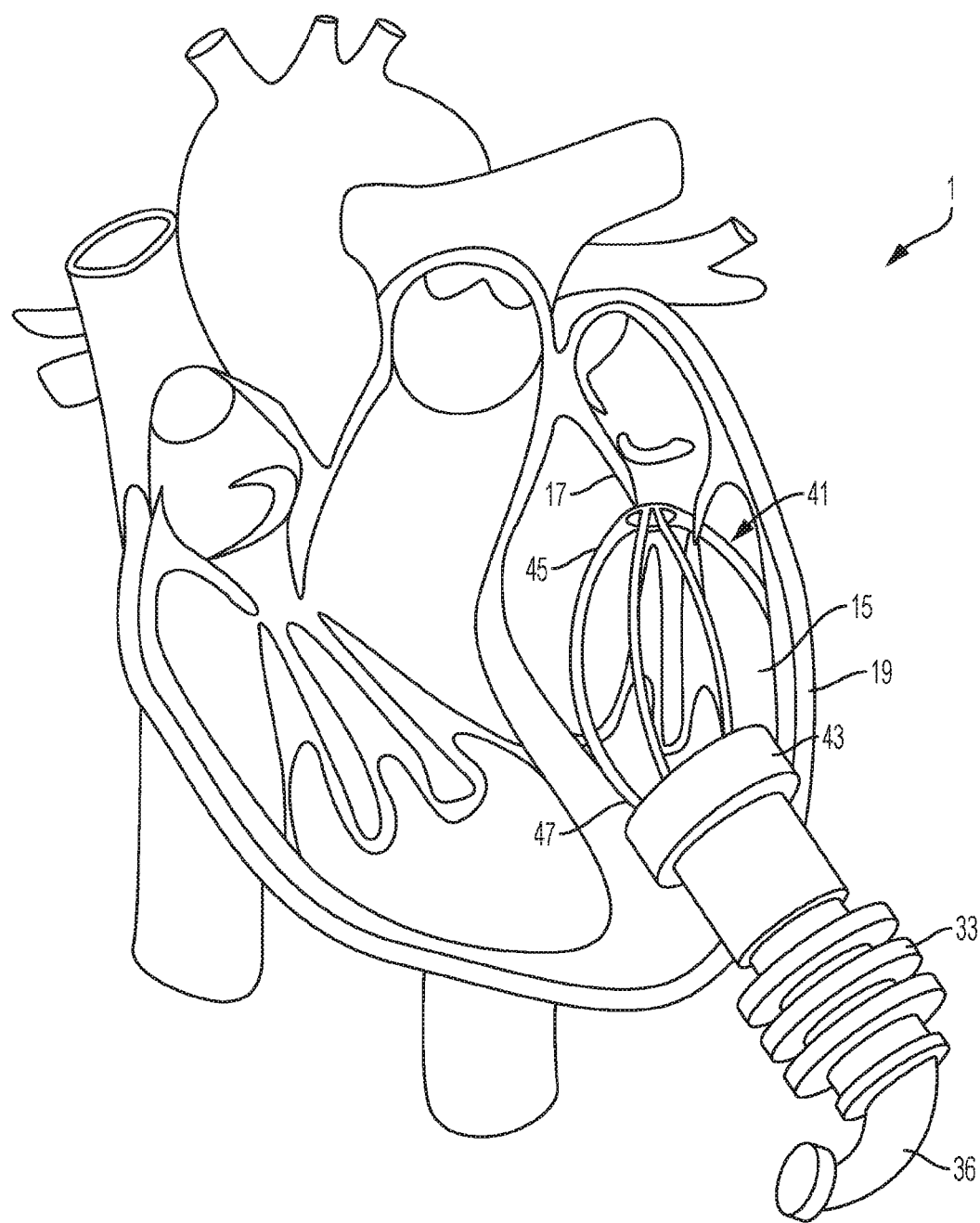
FIG. 4 schematically illustrates a heart with a ventricular assist device (VAD) stent according to an aspect of an embodiment of the present invention.

FIGS. 3 and 4 illustrate an aspect of an embodiment of a stent 41 for use in a heart 1. The stent 41 comprises, but is not limited to a cage or a whisk. As illustrated in FIGS. 3 and 4, the stent 41 may implanted in the LV 15, and may be in partial or substantial contact with portions of an inner surface of the walls of the LV 15. In an aspect of an embodiment, the stent 41 provides sufficient force to prevent collapse of the walls of the LV 15. In another aspect of an embodiment, the stent 41 provides sufficient force to prevent collapse of the walls of the LV 15 and to reduce the incidence of deformation of the walls of the LV 15. This force may serve to ameliorate one or more of the problems of ventricular collapse, suction events, poor alignment of the cannula 32 in the heart 1, atrophy of a portion of the heart 1, adverse remodeling of the heart 1, and ingrowth of heart tissue.

As shown in FIGS. 3 and 4, in an embodiment of the stent 41, the size and shape of the stent 41 may be configured so as to maintain substantial or partial alignment of the direction of flow of blood out of the mitral valve 17 of the heart 1 with the direction of flow of blood into the cannula 43. In an embodiment, the stent 41 may interface with the mitral valve 17. The stent 41 may interface with mitral valve 17 by holding it substantially or partially open. The stent 41 may interface with mitral valve 17 by contacting a portion of the mitral valve 17 or a portion of the heart proximate to the mitral valve 17 such that the position of the stent 41 is held substantially constant relative to the mitral valve 17. These configurations of the stent 41 may serve to ameliorate one or more of the problems of ventricular collapse, suction events, poor alignment of the cannula 32 in the heart 1, atrophy of a portion of the heart 1, adverse remodeling of the heart 1, and ingrowth of heart tissue. While FIGS. 3 and 4 depict implantation of stent 41 in the LV 15 of the heart 1, it should be understood that that the stent 41 can be implanted into another region of the heart 1 such as the right ventricle or an atrium.

In an embodiment, the stent 41 may have a proximal end 45 opposite the cannula 32 and/or the sewing ring 43. In a further embodiment, the stent 41 may have a distal end 47 adjacent to or inside of the cannula 32 and/or the sewing ring 43. The distal end 47 may be inside the cannula 32. The distal end 47 may be one of affixed to the cannula 32 using a suitable connection means. In an alternative embodiment, the distal end 47 may interface with but may not be affixed to the cannula 32.

In an alternative embodiment, the distal end 47 may be outside of the cannula 32 and/or distal end 47 may be affixed to the top or outside of the cannula 32 using suitable connection means. In an alternative embodiment, the distal end 47 may interface with but may or may not be affixed to the cannula 32, and may surround in part the cannula 32 or sit a distance above the cannula 32. The abovementioned configurations of the proximal end 45 and the distal end 47 of the stent 41 may assist in ameliorating one or more of the problems of ventricular collapse, suction events, poor alignment of the cannula 32 in the heart 1, atrophy of a portion of the heart 1, adverse remodeling of the heart 1, and ingrowth of heart tissue.

Figure 7:
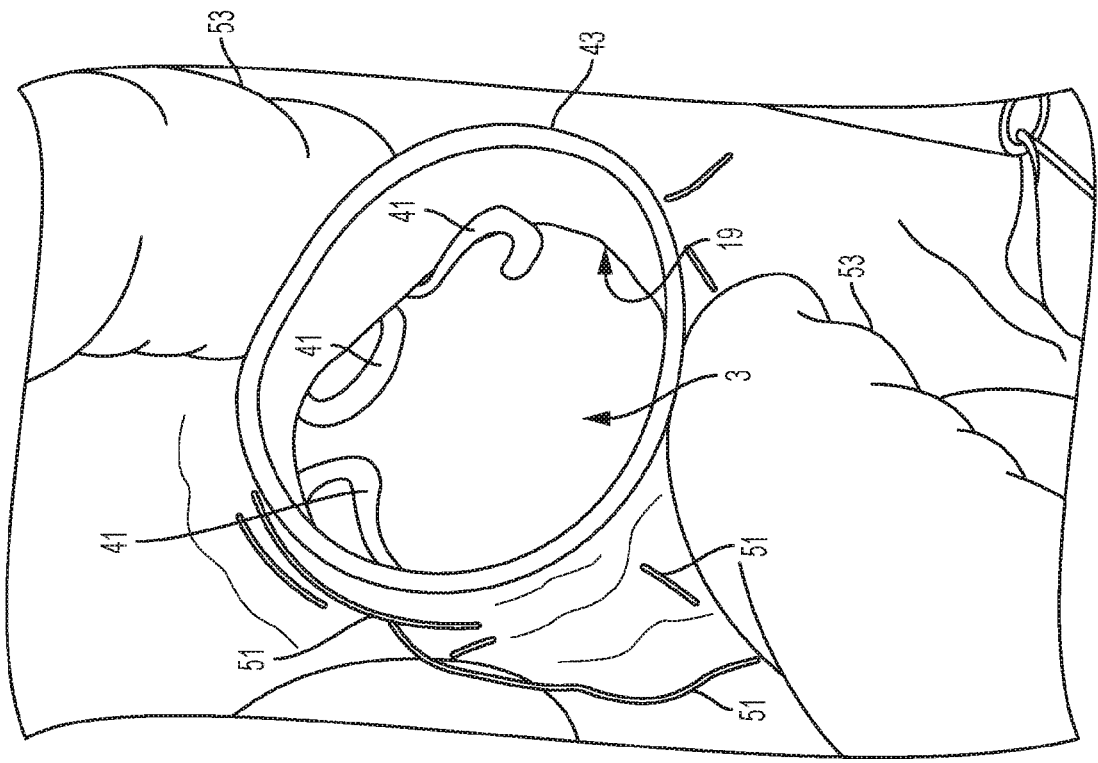
FIG. 7 schematically illustrates a ventricle of a heart supported by a ventricular assist device VAD stent according to an aspect of an embodiment of the present invention.

FIGS. 6 and 7 illustrate a beneficial aspect of the stent 41. As discussed above, FIG. 6 illustrates a collapsed LV 4 as viewed through the sewing ring 43, which is affixed to the heart using sutures 41. FIG. 7 illustrates an open LV 4 assisted with an embodiment of a stent 41. The stent 41 is placed substantially inside the LV such that the LV is in an open state LV 4. In the open state, the LV walls 19 are prevented from collapsing by the stent 41. In particular, as shown in FIG. 7, the stent may provide sufficient force to prevent collapse of the walls of the LV 4. As discussed above, the force, structure, and positioning of the stent 41 may ameliorate one or more of the problems of ventricular collapse, suction events, poor fluid dynamics in the LV 4, atrophy of a portion of the heart 1, adverse remodeling of the heart 1, and ingrowth of heart tissue. FIG. 7 further illustrates the fingers of a surgeon or other medical professional 53 holding the sewing ring 43 after implantation of the stent 41.

Figure 8:
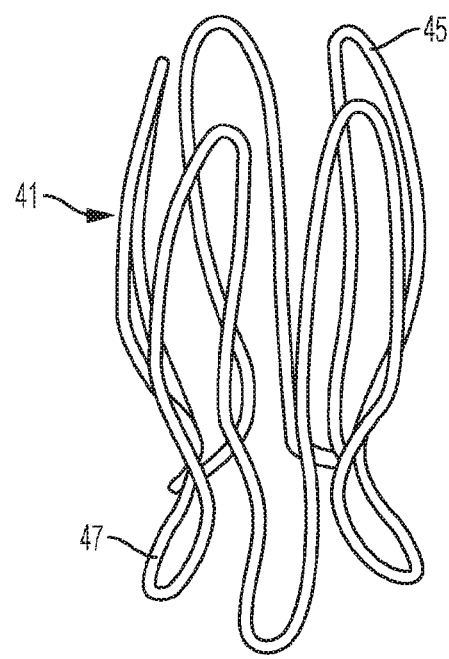
FIG. 8 schematically illustrates a ventricular assist device (VAD) stent according to an aspect of an embodiment of the present invention.
Figure 9:
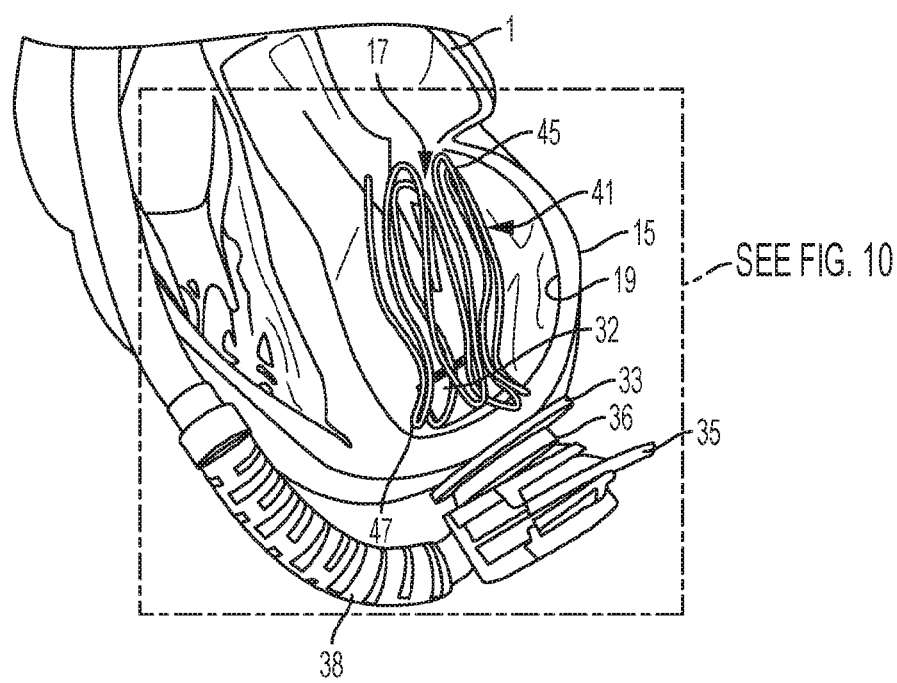
FIG. 9 schematically illustrates a heart with a ventricular assist device (VAD) stent according to an aspect of an embodiment of the present invention.
Figure 10:
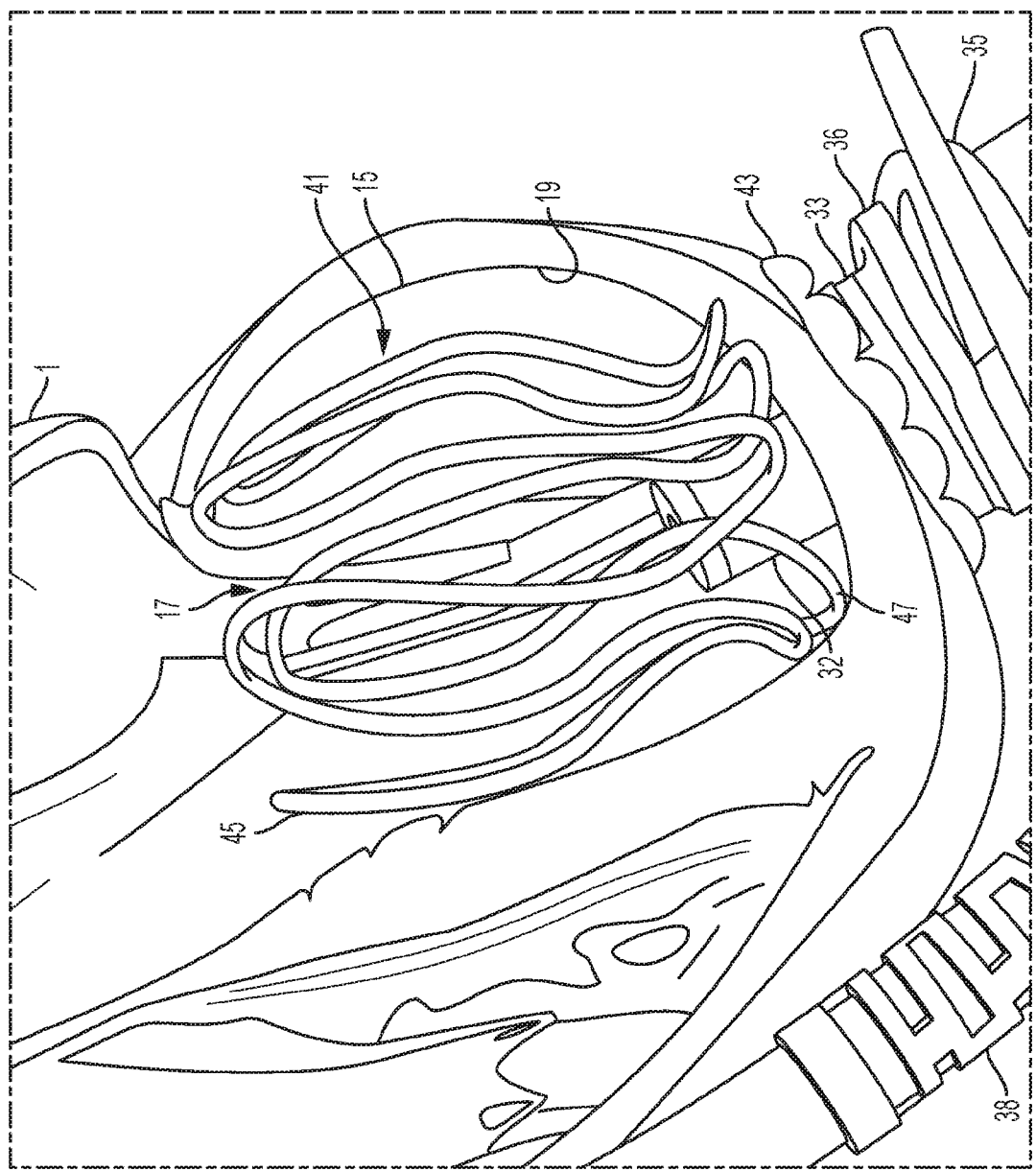
FIG. 10 schematically illustrates an enlarged partial view of a heart shown in FIG. 9 with a ventricular assist device (VAD) stent according to an aspect of an embodiment of the present invention.

FIG. 8 illustrates an embodiment of stent 41. The stent 41 may be formed by a single wire or multiple connected wires. The wire may comprise a plurality of wires connected to form the stent 41. FIGS. 9 and 10 illustrate an embodiment of the stent 41 of FIG. 8 implanted into a LV 15 of a heart 1. The stent 41 may be in partial or substantial contact with portions of an inner surface of the walls of the LV 15. The stent 41 may have a proximal end 45 adjacent to the mitral valve 17. In a further embodiment, the stent 41 may have a distal end 47 adjacent the cannula 32. As shown in FIGS. 9 and 10, the distal end 47 may be in a flared configuration substantially surrounding a portion of the cannula 32. This flared configuration may serve to reduce ingrowth on the cannula 32. This flared configuration may also serve to maintain the position of the stent 41 and/or maintain the alignment of the inflow cannula 32 with the mitral valve 17 so as to reduce the incidence of turbulent flow. In particular, the flared configuration of the distal end 47 of the stent 41, along with the open proximal end 45 and the open channel design through which blood can flow has been shown to avoid problems of turbulent flow. Importantly, flow rates and velocities are do not significantly change when the VAD 31 is used with, or without the stent 41. The configuration, size, positioning, rigidity, and material of the stent 41 may serve to ameliorate one or more of the problems of ventricular collapse, suction events, poor alignment of the cannula 32 in the heart 1, atrophy of a portion of the heart 1, adverse remodeling of the heart 1, and ingrowth of heart tissue.

In an embodiment of the stent 41, the size and shape of the stent 41 may be configured so as to maintain substantial or partial alignment of the direction of flow of blood out of the mitral valve 17 of the heart 1 with the direction of flow of blood into the cannula 43. In an embodiment, the stent 41 may interface with the mitral valve 17. The stent 41 may interface with mitral valve 17 by holding it substantially or partially open. The stent 41 may interface with mitral valve 17 by contacting a portion of the mitral valve 17 or a portion of the heart proximate to the mitral valve 17 such that the position of the stent 41 is held substantially constant relative to the mitral valve 17. These configurations of the stent 41 may serve to ameliorate one or more of the problems of ventricular collapse, suction events, poor alignment of the cannula 32 in the heart 1, atrophy of a portion of the heart 1, adverse remodeling of the heart 1, and ingrowth of heart tissue.

In an aspect of an embodiment, the stent 41 provides sufficient force to prevent collapse of the walls of the LV 15. In another aspect of an embodiment, the stent 41 provides sufficient force to prevent collapse of the walls of the LV 15 and to reduce the incidence of deformation of the walls of the LV 15. While FIGS. 9 and 10 illustrate an aspect of an embodiment where implantation of the stent 41 in the LV 15 of the heart 1, it should be understood that that the stent 41 can be implanted into another region of the heart 1 such as the right ventricle or an atrium. The force exerted by the stent 41 may serve to ameliorate one or more of the problems of ventricular collapse, suction events, poor alignment of the cannula 32 in the heart 1, atrophy of a portion of the heart 1, adverse remodeling of the heart 1, and ingrowth of heart tissue.

Figure 12:
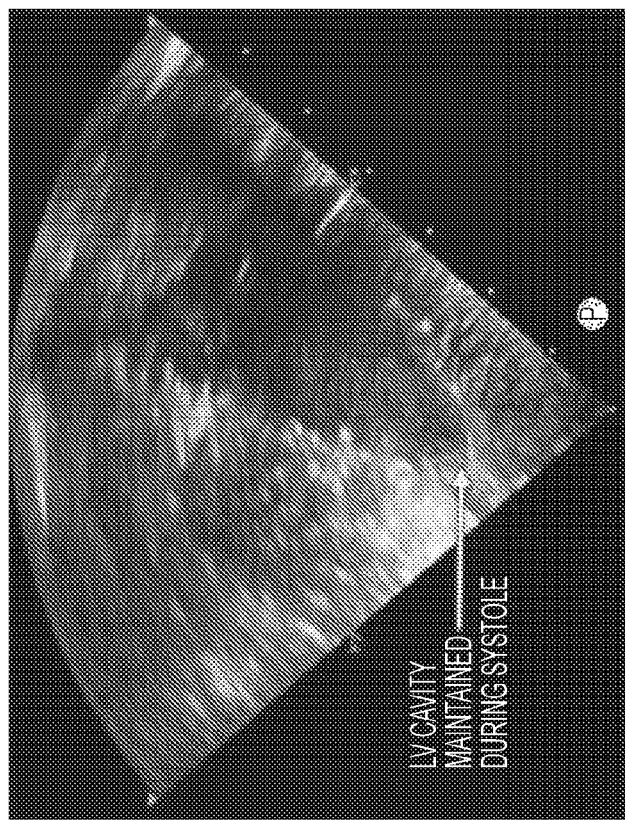
FIG. 12 graphically illustrates graphically illustrates an epicardial echocardiogram of a left ventricle during use of a ventricular assist device (VAD) with a stent according to an aspect of an embodiment of the present invention.
Figure 11:
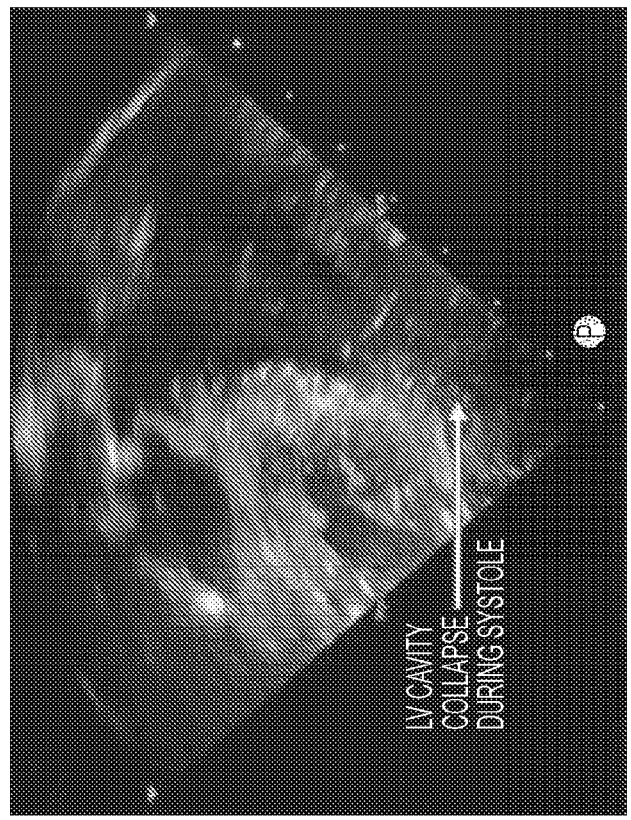
FIG. 11 graphically illustrates an epicardial echocardiogram of a collapsed left ventricle during use of a ventricular assist device (VAD) without a stent.

FIGS. 11-12 illustrate experimental results of echocardiograms of induced suction events in a heart assisted by a left VAD. Adult swine on cardiopulmonary bypass (CPB) underwent implantation of a VAD with the outflow cannula anastomosed end-to-side to the ascending aorta using a partially occluding vascular clamp. A ventriculotomy was made in the left ventricular apex, the sewing ring was placed, and the inflow cannula was secured. After de-airing, CPB was weaned, and the animal was maintained on full VAD support. The flow was increased until a suction event was induced. Next, an intraventricular stent was placed with repeated attempts to induce suction events. Epicardial echocardiogram was used to monitor ventricular collapse and record stent performance.

After implantation, the device speed was increased to 9,500 rpm with a power of 4.0 and a power index of 3.0. These settings reproducibly collapsed the ventricle and stopped flow to the pump creating suction events that were documented on epicardial echocardiogram. In FIG. 11, no stent is used, and the left ventricle is seen in a collapsed state. Following deployment of the intraventricular stent, several attempts at induction of suction events with the same parameters (9500 rpm, 4.0 power, 3.0 power index) were unsuccessful. FIG. 12 illustrates an echocardiogram of this failure to collapse after placement of the stent at the same device parameters. Importantly, no ventricular arrhythmias or hemolysis was noted with placement of the intraventricular stent into the left ventricle during this experiment. Additionally, there was no evidence of cavitation in the pulmonary veins during suction events.

Figure 14:
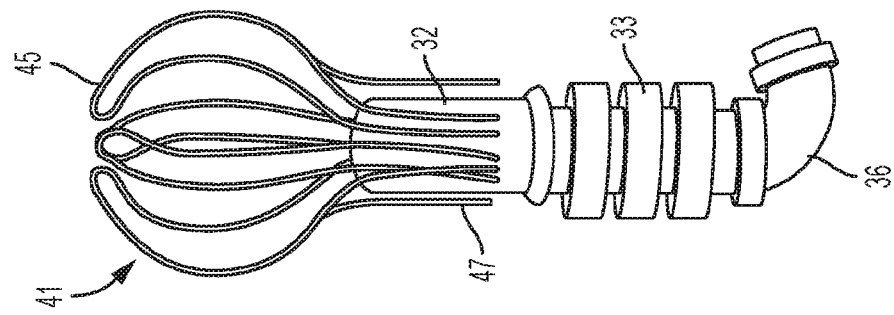
FIG. 14 schematically illustrates a ventricular assist device (VAD) stent in an open configuration (deployed) according to an aspect of an embodiment of the present invention.
Figure 13:
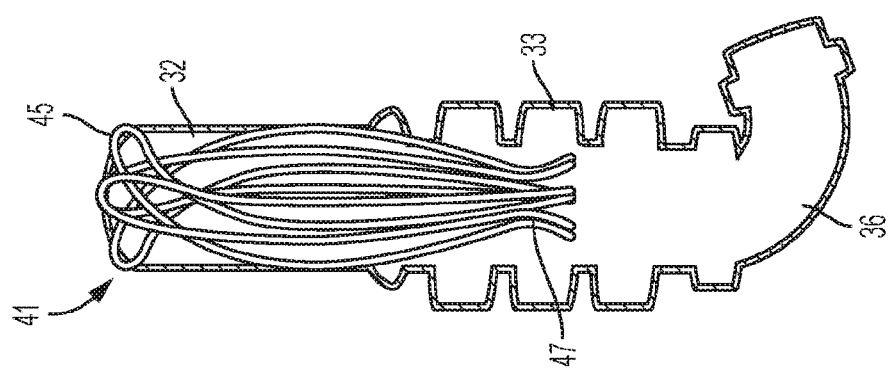
FIG. 13 schematically illustrates a ventricular assist device (VAD) stent in a collapsed configuration (non-deployed) according to an aspect of an embodiment of the present invention.

FIGS. 13 and 14 illustrate an aspect of an embodiment of the invention wherein the stent 41 is transferable between a first compact configuration and a second open configuration. The stent 41 has a proximal end 45 and a distal end 47. As shown in FIG. 13, the stent 41 may be configured to be in a first compact position. This first compact position may allow the stent 41 to fit inside and be transferable through the cannula 32, the manifold 33, the inflow conduit 36, and/or any other suitable VAD component. Alternatively, the stent 41 in the first compact position may be deployable through a sewing ring. Either configuration provides for easy implantation of the stent 41 into a ventricle or atrium of a heart.

FIG. 14 illustrates an aspect of an embodiment wherein the stent 41 has been transferred to a second open configuration. In the second open configuration, at least a portion of the stent 41 has a diameter larger than the diameter of the cannula 32. In an aspect of an embodiment, the distal end 47 of the stent 41 interface with the cannula 32. In an aspect of an embodiment, the interfacing may comprise affixing at least a portion of the distal end to at least a portion of the cannula 32. In another aspect of an embodiment, the interfacing comprises the distal end 47 in a flared configuration sitting outside and substantially surrounding a portion of the cannula 32. This flared configuration may serve to reduce ingrowth on the cannula 32. This flared configuration may also serve to maintain the position of the stent 41 and/or maintain the alignment of the inflow cannula 32 with the mitral valve 17 so as to reduce the incidence of turbulent flow. The configuration, size, positioning, rigidity, and material of the stent 41 may serve to ameliorate one or more of the problems of ventricular collapse, suction events, poor alignment of the cannula 32 in the heart 1, atrophy of a portion of the heart 1, adverse remodeling of the heart 1, and ingrowth of heart tissue.

While FIG. 14 illustrates an aspect of an embodiment wherein the stent 41 in a second open configuration comprises a distal end 47 is in a flared configuration outside of the cannula 32, it should be understood that the distal end 47 may be in an alternative configuration. It should be understood that the distal end 47 may be at least partially inside of the cannula 32. It should also be understood that the distal end 47 may or may not comprise a flared configuration. It should also be understood that the flared configuration might comprise the distal end 47 in a configuration substantially parallel to the cannula 32, or in a configuration that is not substantially parallel to the cannula 32. It should also be understood that the distal end 47 or another portion of the stent 41 may or may not be affixed to a portion of the cannula 32, or any other suitable component of the VAD when the stent 41 is in the first configuration, the second configuration, or both. It should also be understood that the stent in the first compact configuration may allow the stent to pass through the inflow cannula 32, a sewing ring, or any other suitable opening into the heart.

Figure 15:
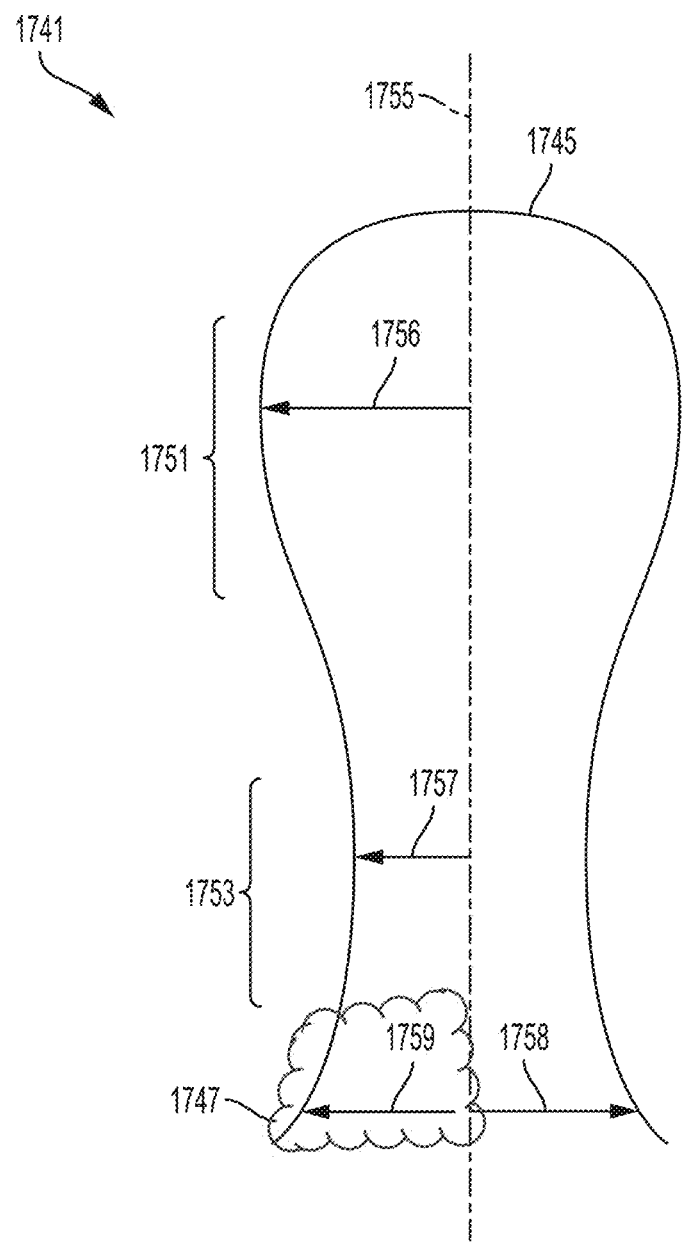
FIG. 15 schematically illustrates a cross section or a contour of a ventricular assist device (VAD) stent according to an aspect of an embodiment of the present invention.

FIG. 15 schematically illustrates a cross section or a contour of a stent 1741 according to an aspect of an embodiment of the present invention. The stent 1741 may comprise a central axis 1755 running along a length of the stent 1741, a distal portion 1747, a proximal portion 1745 opposite the distal portion 1747. The distal portion 1747 may have a minimum radius 1758 from the central axis 1755 and maximum radius 1759 from the central axis 1755, and a first center portion 1751 and a second center portion 1753. The first center portion 1751 may have a minimum radius 1756 from the central axis 1755. The second center portion 1753 may have a maximum radius 1757 from the central axis 1755. The first center portion 1751 and the second center portion 1753 may be in between the distal portion 1747 and the proximal portion 1745 along the central axis 1755. The first center portion 1751 may be adjacent to the proximal portion 1745 and the second center portion 1753 may be adjacent to the distal portion 1747. The maximum radius 1757 of the second center portion 1753 from the central axis 1755 may be smaller than the minimum radius 1756 from the central axis 1755 of the first center portion 1751 and a minimum radius 1758 of the distal portion 1747 such that the distal portion 1747 is in a flared configuration. It should be understood that the distal portion 1747 in a flared configuration may comprise a distal portion 1747 that is substantially parallel to the central axis 1755, or a distal portion 1747 that is not substantially parallel to the central axis 1755. It should also be understood that the proximal portion 1745 may or may not comprise a closed proximal portion 1745 wherein two sides or edges of the stent 1741 meets at or near the central axis 1755.

While the present invention has been described with respect to specific embodiments, it should be understood many modifications, variations, alterations, substitutions, and equivalents would be apparent to those skilled in the art. For example, while the stent 41 or 1741 may comprise a wire, it may also comprise a plurality of wires. The plurality of wires may be connected or stabilized by any suitable connection or stabilization means. The wire or wires may be configured to reduce the incidence of thrombosis. The stent 41 or 1741 may be configured as a cage comprising a plurality of support elements. The stent 41 or 1741 may be manufactured through any suitable manufacturing means such as a casting, bending, molding, depositing, 3D printing, or combination of such methods or any other suitable manufacturing means.

The stent 41 or 1741 may comprise nickel-titanium alloy, stainless steel, silicone, polyester, PTFE, polypropylene, or any other suitable material for use in a human heart. In an aspect of an embodiment, the material of the stent 41 or 1741 may be selected to reduce the risk of thrombosis, to provide adequate force as discussed above, and/or to allow the stent 41 or 1741 to transition between a first compact configuration and a second open configuration.

While the stent 41 or 1741 has been described with respect to specific shapes, contours, and geometries, it should be understood that such shapes, contours, and geometries may be varied. For example, flares may or may not be implemented at either end of the stent 41 or 1741. The wires or components of the stent 41 or 1741 may or may not connect to one another at either or both ends of the stent 41 or 1741. In order to minimize damage to the ventricular walls, the stent 41 or 1741 may have smooth, rounded edges and a small interface with the ventricular walls.

Additionally, the stent 41 or 1741 may provide at least 65 mmHg of force, at least 70 mmHg of force, at least 80 mmHg of force, at least 90 mmHg of force, or at least 100 mmHg of force when used in the heart. The stent may be optimized in size, configuration, and force so as to be better suited for an individual patient or class of patients.

When implanted into a heart, the stent 41 or 1741 may or may not maintain partial substantial contact with the inner walls of the heart. The stent 41 or 1741 may or may not interface with a valve such as the mitral valve of the heart as described herein, or a tricuspid valve if placed on the right side of the heart. The stent 41 or 1741 may or may not interface with the cannula 32 as described herein. A person having skill in the art would understand that there are other applications of the stent that could interface with an aortic or pulmonary valve.

The stent 41 or 1741 may or may not be implanted by passing the stent 41 or 1741 through a sewing ring, cannula, or other appropriate entry point into the heart including a percutaneous catheter-based approach gaining access transseptal. The stent 41 or 1741 may be implanted using a balloon or any other suitable implantation method as well as a self-expanding device. The stent 41 or 1741 may or may not be transferred between a first compact configuration and a second open configuration during or after implantation. The transference between the first and second configurations may automatic or facilitated by human interaction such as release of a maintaining element, application of heat, or active manipulation of the stent.

The features of the stent 41 or 1741 disclosed herein will revolutionize VAD technology and ameliorate the aforementioned problems when implemented in, for example, a right or left ventricle or an atrium of the heart 1. It will also expand its application to pediatric patients, where position is of paramount importance and where use of the stent will make placement easier.

An aspect of various embodiments of the present invention may be utilized for a number of products and services, such as providing for, but not limited thereto, major commercial implications for use in right ventricular assist devices and devices in the atria. An aspect of various embodiments of the present invention would allow VAD technology to leap forward and offer options for patients with severe right-sided heart failure and also into the pediatric population.

It should be appreciated that the related components or portions of the related components (e.g., stent components) as discussed herein may take on all shapes along the entire continual geometric spectrum of manipulation of x, y and z planes to provide and meet the anatomical, environmental and structural demands, operational requirements, and surgical needs (both in pre-deployed, partially deployed, and fully deployed states). Size and shape of the cage during the various stages of deployment (non-deployed, partially deployed, and fully deployed, for example) could also be manipulated by varying the compliance of the stent body and expansion pressure, etc.

It should be appreciated that various sizes, dimensions, contours, rigidity, shapes, flexibility and materials of any of the components or portions of components in the various embodiments discussed throughout may be varied and utilized as desired or required. For example, the sizes, dimensions, contours, rigidity, shapes, flexibility, and materials may be specifically designed for use with a particular patient or for a specific class of patients with similarly sized, developed, limited, and/or malformed hearts and/or cardiovascular systems. Similarly, locations and alignments of the various components may vary as desired or required.

Any of the components (sub-components) or modules disclosed herein may be a variety of widths, lengths, rigidity, firmness, and flexibility, open cellular structure density, as desired or required for operational and anatomical purposes.

The stent (or its sub-components) may have a variety of different degree of open cellular structure density so as to allow the blood to flow and maintain heart geometry to a level that is desired or required for operational and anatomical purposes. The stent (or its sub-components) may have a variety of different degree of open cellular structure density so as to ensure optimizing heart geometry and flow properties, and/or providing a barrier to prevent ingrowth.

The stent (or its sub-components) may have a variety of different degree of rigidity, firmness, and flexibility to maintain heart geometry to a level that is desired or required for operational and anatomical purposes. The stent (or its sub-components) may have a variety of different degree of rigidity, firmness, and flexibility to ensure optimizing heart geometry and flow properties, and/or providing a barrier to prevent ingrowth.

It should be appreciated that any of the components or modules referred to with regards to any of the present invention embodiments discussed herein, may be integrally or separately formed with one another. Further, redundant functions or structures of the components or modules may be implemented.

It should be appreciated that as discussed herein, a subject may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to human (e.g. rat, dog, pig, monkey), etc. It should be appreciated that the subject may be any applicable human patient, for example.

EXAMPLES

Practice of an aspect of an embodiment (or embodiments) of the invention will be still more fully understood from the following examples and experimental results, which are presented herein for illustration only and should not be construed as limiting the invention in any way.

Example 1. A method of assisting a heart for the operation of a ventricular assist device. The method may comprise the steps of: implanting a cannula to the heart; and deploying a stent within a left ventricle, right ventricle, left atrium, or right atrium of the heart.

Example 2. The method of Example 1, wherein step of implanting the cannula to the heart further comprises affixing a sewing ring to the heart.

Example 3. The method of Example 2, wherein step of deploying the stent within the left ventricle, right ventricle, left atrium, or right atrium of the heart further comprises deploying the stent through the sewing ring.

Example 4. The method of Example 1 (as well as subject matter of one or more of any combination of examples 2-3, in whole or in part), wherein the step of deploying the stent within the left ventricle, right ventricle, left atrium, or right atrium of the heart further comprises deploying the stent through the cannula.

Example 5. The method of Example 4, wherein the stent is connected to or remains connected to the cannula after the step of deploying the stent through the cannula.

Example 6. The method of Example 4 (as well as subject matter of one or more of any combination of examples 2-3 and 5, in whole or in part), wherein the stent is not connected to the cannula after the step of deploying the stent through the cannula.

Example 7. The method of Example 1 (as well as subject matter of one or more of any combination of examples 2-6, in whole or in part), wherein the step of deploying the stent within the left ventricle, right ventricle, left atrium, or right atrium of the heart further comprises deploying the stent in a first compact configuration and then expanding the stent to a second open configuration.

Example 8. The method of Example 7, wherein the stent in the second open configuration is configured to do one or more of any combination of the following: cause the cannula to maintain better alignment with a mitral, aortic, pulmonary or tricuspid valve; obstruct the collapse of the left ventricle so as to prevent suction events; reduce adverse remodeling of a right valve of the heart; or reduce ingrowth of heart tissue on the cannula.

Example 9. The method of Example 8, wherein the step of deploying the stent within the left ventricle, right ventricle, left atrium, or right atrium of the heart further comprises deploying a proximal portion of the stent adjacent to the mitral valve of the heart and a distal portion of the stent adjacent to the cannula, and wherein the distal portion of the stent has a flared portion which is maintained outside of the cannula.

Example 10. The method of Example 1 (as well as subject matter of one or more of any combination of examples 2-9, in whole or in part), wherein the step of deploying the stent within the left ventricle, right ventricle, left atrium, or right atrium of the heart further comprises deploying a proximal portion of the stent adjacent to the mitral valve of the heart and a distal portion of the stent adjacent to the cannula, and wherein the distal portion of the stent has a flared portion which is maintained outside of the cannula.

Example 11. The method of Example 1 (as well as subject matter of one or more of any combination of examples 2-10, in whole or in part), wherein the stent comprises a wire.

Example 12. The method of Example 1 (as well as subject matter of one or more of any combination of examples 2-11, in whole or in part), wherein the stent comprises nickel-titanium alloy, stainless steel, silicone, polyester, PTFE, or polypropylene.

Example 13. A stent for assisting a heart during operation of a ventricle assist device. The stent may comprise: a central axis running along a length of the stent; a distal portion; a proximal portion opposite the distal portion, wherein said distal portion having a minimum radius from the central axis; and a first center portion and a second center portion, wherein said first center portion having a minimum radius from the central axis and wherein said second center portion having a maximum radius from the central axis. And wherein: the first center portion and the second center portions are in between the distal portion and the proximal portion along the central axis; the first center portion is adjacent to the proximal portion and the second center portion is adjacent to the distal portion; and the maximum radius of the second center portion from the central axis is smaller than the minimum radius from the central axis of the first center portion and the minimum radius of the distal portion such that the distal portion is in a flared configuration.

Example 14. The stent of Example 13, wherein a maximum radius of the distal portion is smaller than the minimum radius of the first center portion.

Example 15. The stent of Example 13 (as well as subject matter in whole or in part of example 14), wherein the stent comprises a wire.

Example 16. The stent of Example 15, wherein the wire is substantially contiguous.

Example 17. The stent of Example 13 (as well as subject matter of one or more of any combination of examples 14-16, in whole or in part), wherein the stent comprises nickel-titanium alloy, stainless steel, silicone, polyester, PTFE, or polypropylene.

Example 18. The stent of Example 13 (as well as subject matter of one or more of any combination of examples 14-17, in whole or in part), wherein the stent is transferable between a first compact position and a second open configuration, wherein the stent has a maximum radius from the central axis in the first compact position such that it is deployable through a cannula of a ventricular assist device or such that it is deployable through a sewing ring affixed to a heart for use with a ventricular assist device.

Example 19. A ventricular assist device. The ventricular assist device may comprise: a cannula for implantation in a heart; and a stent for deployment in a left ventricle, a right ventricle, a left atrium, or a right atrium of the heart.

Example 20. The ventricular assist device of Example 19, wherein the stent is affixed to the cannula.

Example 21. The ventricular assist device of Example 19 (as well as subject matter in whole or in part of example 20), wherein the stent is not affixed to the cannula.

Example 22. The ventricular assist device of Example 19 (as well as subject matter of one or more of any combination of examples 20-21, in whole or in part), wherein the stent may comprise: a central axis running along a length of the stent; a distal portion; a proximal portion opposite the distal portion, wherein said distal portion having a minimum radius from the central axis; and a first center portion and a second center portion, wherein said first center portion having a minimum radius from the central axis and wherein said second center portion having a maximum radius from the central axis. And wherein: the first center portion and the second center portions are in between the distal portion and the proximal portion along the central axis; the first center portion is adjacent to the proximal portion and the second center portion is adjacent to the distal portion; and the maximum radius of the second center portion from the central axis is smaller than the minimum radius from the central axis of the first center portion and the minimum radius of the distal portion such that the distal portion is in a flared configuration.

Example 23. The stent of Example 19 (as well as subject matter of one or more of any combination of examples 20-22, in whole or in part), wherein the stent comprises a wire.

Example 24. The stent of Example 23 (as well as subject matter of one or more of any combination of examples 20-23, in whole or in part), wherein the wire is substantially contiguous.

Example 25. The stent of Example 19 (as well as subject matter of one or more of any combination of examples 20-24, in whole or in part), wherein the stent is comprises nickel-titanium alloy, stainless steel, silicone, polyester, PTFE, or polypropylene.

Example 26. The stent of Example 19 (as well as subject matter of one or more of any combination of examples 20-25, in whole or in part), wherein the stent is transferable between a first compact position and a second open configuration, wherein the stent has a maximum radius from the central axis in the first compact position such that it is deployable through the cannula or such that it is deployable through a sewing ring affixed to the heart for use with the ventricular assist device.

Example 27. The stent of Example 26, wherein the stent in the second open configuration is configured to do one or more of any combination of the following: cause the cannula to maintain better alignment with a mitral valve of the heart; obstruct the collapse of the left ventricle so as to prevent suction events; reduce adverse remodeling of a right valve of the heart; or reduce ingrowth of heart tissue on the cannula.

Example 28. The method of using any of the devices, systems, assemblies, or their components provided in any one or more of examples 1-27.

Example 29. The method of providing instructions to use or operate of any of the devices, systems, assemblies, or their components provided in any one or more of examples 1-27.

Example 30. The method of manufacturing any of the devices, systems, assemblies, or their components provided in any one or more of examples 1-27.

Example 31. It is noted that machine readable medium or computer useable medium may be configured to execute the subject matter pertaining to system or related methods disclosed in examples 1-27, as well as examples 28-30.

Example 32. A stent for assisting a heart during operation of a ventricle assist device, wherein said stent is configured to be transferable between a compact position and an expanded position. Further, wherein when said stent is in said expanded position, said stent comprises: a central axis running along a length of the stent; a distal portion; a proximal portion opposite the distal portion, wherein said distal portion having a minimum radius from the central axis; and a first center portion and a second center portion, wherein said first center portion having a minimum radius from the central axis and wherein said second center portion having a maximum radius from the central axis and, wherein: a) the first center portion and the second center portions are in between the distal portion and the proximal portion along the central axis; b) the first center portion is adjacent to the proximal portion and the second center portion is adjacent to the distal portion; and c) the maximum radius of the second center portion from the central axis is smaller than the minimum radius from the central axis of the first center portion and the minimum radius of the distal portion such that the distal portion is in a flared configuration. Further, wherein when said stent is in said expanded position, said stent comprises: a) wherein said stent is configured to be disposed in a left ventricle, right ventricle, left atrium, or right atrium of the heart; and b) wherein said proximal portion of said stent is configured to be both adjacent to and outside said mitral valve, aortic valve, pulmonary valve or tricuspid valve without passing an annulus of any of said respective valves.

REFERENCES

The devices, systems, apparatus, materials, compositions, components, computer readable medium, computer processors, and methods (of manufacture and use) of various embodiments of the invention disclosed herein may utilize aspects disclosed in the following references, applications, publications and patents and which are hereby incorporated by reference herein in their entirety (and which are not admitted to be prior art with respect to the present invention by inclusion in this section):

1. U.S. Patent Application Publication No. US 2005/0033107 A1, Tsubouchi, T., "Adjustable Coupling Mechanism for the Conduit on a Ventricular Assist Device", Feb. 10, 2005.
2. International Patent Application Publication No. WO 2014/207225 A1, Halvorsen, P., et al., "Monitoring of a Cardiac Assist Device", Dec. 31, 2014.
3. U.S. Patent Application Publication No. US 2015/0306290 A1, Rosenberg, et al., "Smart Tip LVAD Inlet Cannula", Oct. 29, 2015.
4. U.S. Patent Application Publication No. US 2008/0306329 A1, Lu, et al., "Ventricular Assist Device", Dec. 11, 2008.
5. International Patent Application Publication No. WO 2014/085806 A1, Rosenberg, G., et al., "Smart Tip LVAD Inlet Cannula", Oct. 29, 2015.
6. Kapelios C J, Charitos C, Kaldara E, Malliaras K, Nana E, Pantsios C, et al. Late-onset right ventricular dysfunction after mechanical support by a continuous-flow left ventricular assist device. J Heart Lung Transplant. 2015; 34 (12):1604-10. □
7. U.S. Pat. No. 6,817,836 B2, Nose, Y., et al., "Methods and Apparatus for Controlling a Continuous Flow Rotary Blood Pump", Nov. 16, 2004.
8. U.S. Patent Application Publication No. US 2006/0241335 A1, Benkowski, R., et al., "Method and System for Physiologic Control of a Blood Pump", Oct. 26, 2006.
9. U.S. Pat. No. 7,284,956 B2, Nose, Y., et al., "Methods and Apparatus for Controlling a Continuous Flow Rotary Blood Pump", Oct. 23, 2007.
10. U.S. Patent Application Publication No. US 2014/0100413 A1, Casas, F., et al., "Suction Detection on an Axial Blood Pump Using BEMF Data", Apr. 10, 2014.
11. U.S. Patent Application Publication No. US 2016/0058930 A1, Medvedev, A., "Blood Pump and Method of Suction Detection", Mar. 3, 2016.
12. U.S. Patent Application Publication No. US 2015/0367048 A1, Brown, M., et al., "Methods and Devices for Identifying Suction Events", Dec. 24, 2015.
13. U.S. Patent Application Publication No. US 2014/0107399 A1, Spence, P., "Devices, Systems and Methods for Facilitating Flow from the Heart to a Blood Pump", Apr. 17, 2014.
14. International Patent Application Publication No. JP 2005080991 A, Nose, Y., et al., "Cannula Chip for Heart Aid Unit", Mar. 31, 2005.
15. U.S. Pat. No. 5,827,171, Dobak, III, et al., "Intravascular Circulatory Assist Device", Oct. 27, 1998.
16. U.S. Pat. No. 6,673,042 B1, Samson, W., "Expandable Venous Cannula and Method of Use", Jan. 6, 2004.
17. U.S. Patent Application Publication No. US 2007/0049787 A1, Nose, Y., et al., "Cannula Tip for a Cardiac Assist Device", Mar. 1, 2007.
18. U.S. Patent Application Publication No. US 2007/0156233 A1, Kapadia, et al., "Percutaneous Atrioventricular Valve and Method of Use", Jul. 5, 2007.
19. U.S. Patent Application Publication No. US 2006/0293698 A1, Douk, N., "Retainer Device for Mitral Valve Leaflets", Dec. 28, 2006.
20. U.S. Patent Application Publication No. US 2007 0244545 A1, Birdsall, et al., Oct. 18, 2007.
21. U.S. Patent Application Publication No. US 2010/0168848 A1, Horvath, et al., Jul. 1, 2010.
22. U.S. Patent Application Publication No. US 2006/0229488 A1, Ayre, et al., "Blood Pressure Detecting Device and System", Oct. 12, 2006.
23. U.S. Pat. No. 7,156,873 B2, Nose, et al., "Methods for Detecting an Abnormal Condition of a Blood Pump System", Jan. 2, 2007.
24. U.S. Pat. No. 7,175,588 B2, Morello, G., "Method and System for Detecting Ventricular Collapse", Feb. 13, 2007.
25. U.S. Pat. No. 7,396,327 B2, Morello, G., "Blood Pump System and Method of Operation", Jul. 8, 2008.
26. International Patent Application Publication No. JP 2005066013 A, Nose, et al., "Method and Apparatus for Controlling Continuous Flow Rotary Blood Pump", Mar. 17, 2015.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

We claim:

1. A stent for assisting a heart during operation of a ventricle assist device, comprising:
    wherein said stent is configured to be transferable between a compact position and an expanded position, wherein when said stent is in said expanded position, said stent comprises:
        a central axis running along a length of the stent;
        a distal portion;
        a proximal portion opposite the distal portion, wherein said distal portion having a minimum radius from the central axis; and
        a first center portion and a second center portion, wherein said first center portion having a minimum radius from the central axis and wherein said second center portion having a maximum radius from the central axis and, wherein:
            the first center portion and the second center portions are in between the distal portion and the proximal portion along the central axis;
            the first center portion is adjacent to the proximal portion and the second center portion is adjacent to the distal portion; and
            the maximum radius of the second center portion from the central axis is smaller than the minimum radius from the central axis of the first center portion and the minimum radius of the distal portion such that the distal portion is in a flared configuration; and
        wherein said stent is configured to be disposed in a left ventricle, right ventricle, left atrium, or right atrium of the heart; and:
        wherein said proximal portion of said stent is configured to be both adjacent to and outside of a mitral valve, an aortic valve, a pulmonary valve or a tricuspid valve without passing an annulus of any of said respective valves.

2. The stent of claim 1, further comprising:
    a kit, wherein said kit comprises the ventricular assist device, wherein said ventricular assist device comprises:
        a cannula of said ventricular assist device for implantation in the heart; and
        said stent is configured for deployment in the left ventricle, right ventricle, left atrium, or right atrium of the heart.

3. The stent of claim 2, wherein the stent comprises a wire.

4. The stent of claim 3, wherein the wire is substantially contiguous.

5. The stent of claim 2, wherein the stent is affixed to the cannula.

6. The stent of claim 2, wherein the stent is not affixed to the cannula.

7. The stent of claim 2, wherein the stent is comprises nickel-titanium alloy, stainless steel, silicone, polyester, PTFE, or polypropylene.

8. The stent of claim 2, wherein the stent has a maximum radius from the central axis in the compact position such that it is deployable through the cannula or such that it is deployable through a sewing ring affixed to the heart for use with the ventricular assist device.

9. The stent of claim 1, wherein the stent comprises a wire.

10. The stent of claim 9, wherein the wire is substantially contiguous.

11. The stent of claim 1, wherein the stent has a maximum radius from the central axis in the compact position such that it is deployable through a cannula of said ventricular assist device or such that it is deployable through a sewing ring affixed to the heart for use with the ventricular assist device.

12. The stent of any one of claim 11 or 8, wherein when the stent is in the expanded position said stent is configured to do one or more of any combination of the following:
    cause the cannula to maintain better alignment with the mitral valve, aortic valve, pulmonary valve, or tricuspid valve of the heart;
    obstruct the collapse of the left ventricle, right ventricle, left atrium, or right atrium so as to prevent suction events;
    reduce adverse remodeling of a right valve of the heart; or
    reduce ingrowth of heart tissue on the cannula.

13. The stent of claim 1, wherein a maximum radius of the distal portion is smaller than the minimum radius of the first center portion.

14. The stent of claim 1, wherein the stent comprises nickel-titanium alloy, stainless steel, silicone, polyester, PTFE, or polypropylene.

15. The stent of claim 1, wherein when the stent is in the expanded position said stent is configured to do one or more of any combination of the following:
- cause a cannula of said ventricular assist device to maintain better alignment with the mitral valve, aortic valve, pulmonary valve, or tricuspid valve of the heart;
- obstruct the collapse of the left ventricle, right ventricle, left atrium, or right atrium so as to prevent suction events;
- reduce adverse remodeling of a right valve of the heart; or
- reduce ingrowth of heart tissue on the cannula.

* * * * *